United States Patent
Lönneker-Lammers (10) Patent No.: US 7,278,962 B2
(45) Date of Patent: Oct. 9, 2007

(54) INCUBATOR FOR NEWBORN AND PREMATURE PATIENTS

(75) Inventor: Torsten Lönneker-Lammers, Hamburg (DE)

(73) Assignee: LMT Lammers Medical Technology GmbH, Lubeck (DE)

( * ) Notice: Subject to any disclaimer, the term of this patent is extended or adjusted under 35 U.S.C. 154(b) by 164 days.

(21) Appl. No.: 11/120,077

(22) Filed: May 2, 2005

(65) Prior Publication Data

US 2005/0192473 A1     Sep. 1, 2005

Related U.S. Application Data

(63) Continuation-in-part of application No. 10/474,016, filed as application No. PCT/EP02/04094 on Apr. 12, 2002, now abandoned.

(30) Foreign Application Priority Data

Apr. 12, 2001  (EP)  .................................. 01109195

(51) Int. Cl.
*A61G 11/00* (2006.01)
(52) U.S. Cl. ...................................... 600/22
(58) Field of Classification Search .................. 600/21, 600/22, 407, 410, 415, 422; 128/205.26; 5/600, 603; 250/515.1–519.1
See application file for complete search history.

(56) References Cited

U.S. PATENT DOCUMENTS

| | | | |
|---|---|---|---|
| 3,329,845 A * | 7/1967 | Lear | 310/256 |
| 4,079,728 A * | 3/1978 | Gatts | 600/22 |
| 4,617,912 A | 10/1986 | Beer et al. | |
| 5,006,105 A * | 4/1991 | Sherard | 600/22 |
| 5,616,115 A * | 4/1997 | Gloyd et al. | 600/22 |
| 5,730,355 A | 3/1998 | Lessard et al. | |
| 5,800,335 A | 9/1998 | Koch et al. | |
| 5,935,055 A | 8/1999 | Koch et al. | |
| 6,611,702 B2 | 8/2003 | Rohling et al. | |
| 2004/0106844 A1* | 6/2004 | Lonneker-Lammers | 600/22 |
| 2005/0113668 A1* | 5/2005 | Srinivasan | 600/411 |

FOREIGN PATENT DOCUMENTS

| | | |
|---|---|---|
| EP | 0 864 295 A2 | 9/1998 |
| JP | 64-86961 | 3/1989 |
| WO | WO98/48756 | 11/1998 |

* cited by examiner

*Primary Examiner*—Samuel G. Gilbert
(74) *Attorney, Agent, or Firm*—Alix, Yale & Ristas, LLP (57) ABSTRACT

An incubator for newborn and premature patients includes an air delivery unit with an electric motor and heating and humidifying devices, a control unit including sensing devices to measure air temperature and humidity and a control panel integrally mounted to the incubator. Sensitive electrical components, such as the electric motor and control unit, are shielded from the magnetic field of the imaging equipment so that the incubator, with its patient, can be placed inside the imaging equipment and remain fully functional. Shielding for the electric motor is constructed of soft magnetic material and arranged to leave a dielectric gap between the shield and the motor.

20 Claims, 6 Drawing Sheets

INCUBATOR FOR NEWBORN AND PREMATURE PATIENTS

CROSS REFERENCE TO RELATED APPLICATIONS

This application is a continuation-in-part of U.S. patent application Ser. No. 10/474,016, filed Oct. 3, 2003 now abandoned, which is the National Stage of PCT/EP02/04094, filed Apr. 12, 2002.

BACKGROUND OF THE INVENTION

1. Field of the Invention

The invention relates to an incubator for newborn and premature patients, which can be introduced into the magnetic field of an NMRI tomograph.

2. Description of the Related Art

Premature and newborn babies are often unable to independently maintain their body temperature. They are therefore kept warm in what are called incubators. These are generally of a considerable size and contain metal parts, in particular iron parts. Such incubators cannot therefore be introduced into the magnetic field of an NMRI tomograph, so that, even though desirable, it is not possible to examine the patient by NMRI while he/she is in the incubator.

An incubator is in fact known with which the patient can be introduced into the magnetic field of the NMRI tomograph (DE 196 17 739 C1). However, said incubator is of a relatively simple design and, for example, has no devices for examining the patient, in particular no coil with which the magnetic resonance signals can be picked up. In addition, said incubator requires a pressure fluid source to operate the ejector for the air circulation and external gas canisters. The incubator is therefore difficult to transport.

An incubator of the type mentioned at the outset (WO 98/48756) does have devices for examining the patient, for example a coil for the magnetic resonance signals. However, the incubator is connected via a plurality of cables and tube lines to a base unit which must be arranged away from the magnetic field, and for this reason it is again very difficult to transport. If an NMR image of the patient is to be taken, this involves the complicated task of bringing the base unit and the incubator to the NMRI tomograph.

A known incubator has a specially designed type of airflow and regulation of this flow, and also of the temperature (U.S. Pat. No. 5,730,355). However, said incubator is obviously not designed for introduction into an NMRI tomograph, so that problems from interaction with the magnetic field and the measurement electronics of an NMRI tomograph cannot arise.

Because of the problems that electric motors and electronic circuits could, on the one hand, have their function disrupted by the magnetic field and could, on the other hand, emit signals which interfere with the signals recorded in the NMRI tomography, it has hitherto been considered necessary to provide the electrical control means and electrical drive mechanism for fans and the like for example, in a separate structural component (EP 0 864 295 A2). Moreover, because these incubators had to be made small, it was hitherto not possible to satisfactorily solve the problem of uniform heat distribution within the patient space. In one of the previously known incubators (DE 196 17 739 C1), there is indeed an effective circulation of air in the double-walled patient-receiving space. However, the small cross section means that, during use with a patient, a uniform distribution of heat and airflow is no longer ensured, which can lead to considerable problems. In the other previously known incubator (WO 98/48756), it is not at all clear how effective the air circulation and replenishment is intended to be and how it is designed.

SUMMARY OF THE INVENTION

An object of the invention is to provide an incubator which is suitable for NMRI tomography, is easy to transport and, despite its small size, permits a uniform temperature distribution and, consequently, effective and gentle heating/temperature maintenance of the patient.

The solution according to aspects of the invention is an incubator including devices for delivery and circulation of fresh air and a drive mechanism for these devices, devices for heating and humidifying the air, for regulating the temperature of said air, and for examining the patient, where the devices are driven electrically and are arranged integrally on the incubator. An aspect of the invention relates to configuring air movement in the patient space to include a component extending in the longitudinal direction of the incubator and a component extending in a cylindrical formation about the longitudinal axis.

According to the invention, therefore, the belief that electrically driven devices cannot be arranged directly on the incubator has been disproven. Thus, for example, the fan no longer needs to be driven by a pressure fluid that is generated separately from the incubator. Instead, it can be driven electrically by a motor that is arranged on the incubator. The patient space is constantly permeated with air that flows in along one entire longitudinal side and forms a cylinder of air about the longitudinal axis of the incubator, and the air is once again suctioned off, on this axis, at one end of the patient space.

The electrical and electronic equipment is configured in such a way that, on the one hand, the measurement results, in particular the signals for the imaging, are influenced to the least possible extent, while, on the other hand, the energy emitted by the tomograph, and its magnetic field, has at the very most a minimal influence on the electrical and electronic equipment of the incubator. In the imaging, the signal/noise ratio and uniformity are important, and interferences caused by shadow images and geometric distortions have to be avoided. Furthermore, the incubator's performance data must not be negatively affected, for example the measurement accuracy and operating stability in the case of processor systems.

These aims are achieved by the combination of different measures, which combination then has the surprising result that all devices for effective functioning of the incubator can be arranged directly on the incubator, with the result that the incubator can be easily transported and introduced into the medical imaging equipment.

For effective shielding, all electrical components are incorporated throughout in protective casings providing good electrical conduction. For example, it is possible to use housings made of aluminum, sheathed lines and cables. Housing apertures, for example for displays, are provided with a metallic braid or metallized foil. Unused connections are covered so as to be EMC-compliant. It is important here that the screening is effected throughout.

With specific reference to any electric motors included on the incubator, the shielding is configured of a soft magnetic material, such as iron or iron alloys. The shielding for the motor is configured as a cylinder with the ends of the cylinder closed by disc-shaped end caps of the soft magnetic material. A dielectric gap is defined between the motor and the shielding to prevent the motor becoming part of the magnetic circuit of the shield. A particularly effective motor shield is provided by inner and outer cylindrical shields that are spaced apart to define a dielectric (air) gap between the inner and outer shields in addition to the dielectric gap between the motor and the inner shield. The motor is supported within the shield by a plastic disc or ring adjacent one of the end caps. In this manner, the motor is effectively isolated from the magnetic field of the medical imaging equipment.

All housing parts must be well grounded and jointly applied to ground potential. A star-shaped connection of the housing parts is important here; in any event, loops must be avoided in the conductor routing.

The electrical signals have to be filtered, and this applies both to the sensors and to the actuators, which are managed by the control system. Accordingly, a decision is made between sensor signals (temperature, humidity, response contacts) and actuation signals (control of heat elements, motors). Suitable filter topologies and filter components are chosen depending on the differentiation. A connection line between two components can be connected to ground via a capacitive filter (capacitor) in order thereby to ground high-frequency signals. Moreover, two components can be connected via a parallel circuit of a capacitor and an inductor, i.e. a suppressor circuit (throttle with small shunt capacitance). This gives a high suppression effect for high outputs/voltages. No current is led off to ground. The components should be of a high quality into the 100 MHz range. Air coils and chip capacitors should be used. For very high demands, an exact balance can be effected by means of a network analyzer.

Finally, ferromagnetic components should be avoided. The use of piezo technology is advisable for switches and drives. A band limit of the processor system (bus, data transfer) is also advisable.

Air is expediently delivered through a channel into a stabilizing space below the lying surface for the patient. After overcoming a flow resistance, the air can then pass with acceleration into the patient space, at a point to the side of the patient, so that the air movement mentioned above takes place. Since the devices of the incubator are electrically driven, an electrical connection simply has to be interrupted and then restored in order to transport the incubator. A transport carriage for the incubator could easily be provided with a battery to provide power to operate the incubator for at least 30 minutes. The supply of heated fresh air to the patient is therefore interrupted for only a very short time when moving the incubator from its stationary position to the transport carriage.

In many cases, it is necessary to supply the patient not just with air, but also with oxygen-enriched air. It is also possible to enrich the air with pure oxygen. In an expedient embodiment, the enrichment with oxygen is automatically regulated in accordance with a set value and monitored.

In an advantageous embodiment, not only is the air temperature regulated, but also the air humidity.

The measurement coil for the NMRI tomography could be arranged in the tomograph in such a way that the incubator has to be pushed into this measurement coil. In a particularly expedient embodiment, however, the measurement coil for the NMRI tomography is arranged in the patient space. In an expedient embodiment, the measurement coil can be adjustable relative to the patient so that different body parts of the patient can be examined. The coil suitable for the particular examination can be inserted through a hatch in an end wall of the incubator housing.

The monitoring of the oxygen concentration in the incubator provides no information on the status of the patient. In addition, oxygen sensors interfere with the imaging. For these reasons, it is expedient to monitor oxygen saturation ($SpO_2$) in the patient by means of known sensors. The incubator is expediently controlled by a microprocessor.

The end faces (end walls) of the patient-receiving enclosure are expediently provided with passages for ventilation lines, anesthesia lines and infusion lines and/or other lines such as a signal cable of the measurement coil.

To ensure that the electronics and the motors are not disturbed by the magnetic field or that these electrical and electronic components do not interfere with the measurement, the electronics are shielded in a suitable way. The voltage for the electronics is supplied using a shielded switched-mode power supply unit, while the power elements (heater, humidifier) are supplied directly with line voltage via a semiconductor relay with the aid of pulse width modulation. The whole incubator is regulated with the aid of a real-time operating system and a software program and, in the event of deviations from the set values, a visual and/or acoustic alarm is emitted as appropriate. The shielding and mechanical structure of the apparatus are such that the incubator is suitable for use in open and for closed tomographs with magnetic fields of 0.2 to 3 Tesla. In addition, the incubator is configured so that it can be carried by two persons and can be moved from a suitable trolley onto the patient support of the tomograph in the tomograph space. The trolley carries the electrical power source in the form of an accumulator, such as a battery pack. If the patient is to be supplied not just with air, but also with oxygen, the corresponding gas canisters are of course also located on the trolley.

The parameters are expediently displayed and set digitally. The relevant international standards for medical appliances are of course also satisfied. Moreover, provision will preferably be made for the fresh air to be delivered through suitable filters, in particular particle filters, in order to avoid contamination of the respiratory air for the patient. As far as is possible, ferromagnetic materials will be avoided not just for the incubator, but also for accessory components. Magnetic materials will also be avoided in the trolley and in the other components such as the power and gas supply. Apertures and fixtures for accessories, for example monitors or ventilation devices, can likewise be provided in the incubator according to the invention.

BRIEF DESCRIPTION OF THE DRAWINGS

The invention is described below on the basis of advantageous embodiments and with reference to the attached drawings, in which.

DETAILED DESCRIPTION OF THE PREFERRED EMBODIMENTS

Figure 1:
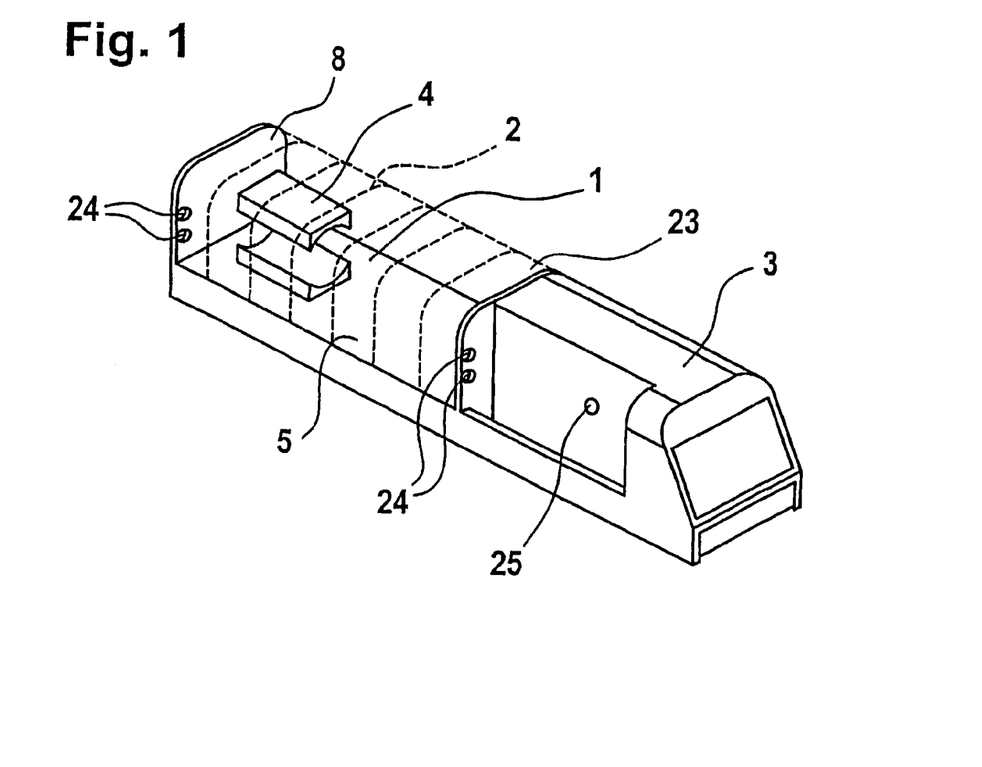
FIG. 1 shows, in a perspective view, a first embodiment of the incubator according to the invention.

A first exemplary incubator according to aspects of the present invention is shown in FIG. 1. The incubator has a patient-receiving space 1 which can be closed off by a hood 2 indicated with broken lines.

The hood 2 has a double wall which, in addition to protecting against radiation losses, also protects the patient from the high noise level of the tomograph. To reduce heat losses when the hood is open, four small hatches 26 (FIG. 8) are integrated into the hood, and access to the patient is possible through these hatches. The air delivery and control unit 3 is situated at one end of the incubator. One or more measurement coils 4 for receiving the signals for the NMRI tomography are provided in the patient space 1, and, at the other end of the patient space 1, there is a hatch 8 for introduction and positioning of the measurement coils 4. The patient lies on a support surface 5. The patient can also be observed through the transparent hatch 8 during the examination in the tomograph.

Figure 2:
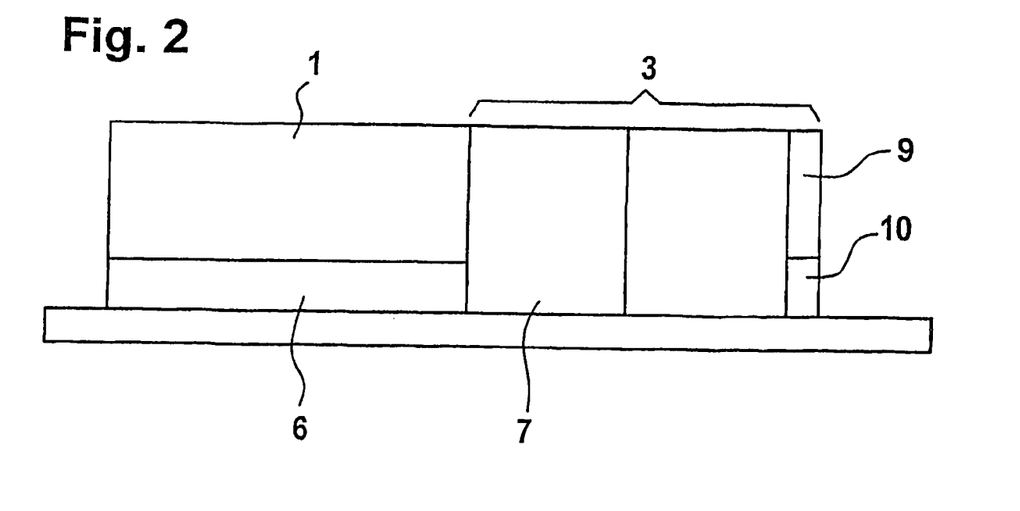
FIG. 2 shows a diagrammatic view of the arrangement of the various components of the incubator according to the invention.

FIG. 2 is a diagrammatic representation showing the structure of the incubator and the arrangement of the individual components. Situated below the receiving space 1 there is an air duct 6 which is supplied with air from a part 7. An control panel 9 and control unit, and connections for electrical power supply and if necessary for oxygen are provided on the part 10.

Figure 3:
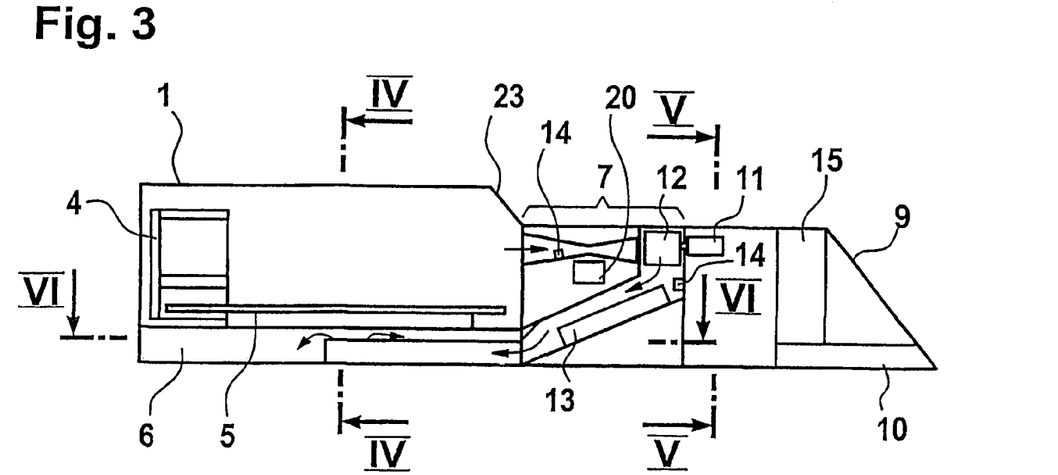
FIG. 3 shows a longitudinal section through a second embodiment of the incubator according to the invention.
Figure 4A:
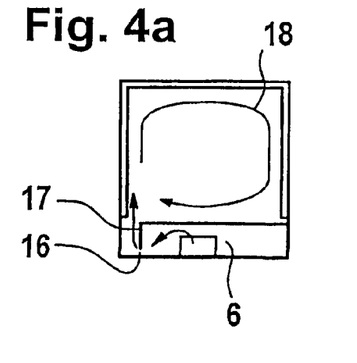
FIG. 4a shows a cross section of a variant a, along the line IV-IV in FIG. 3.
Figure 4B:
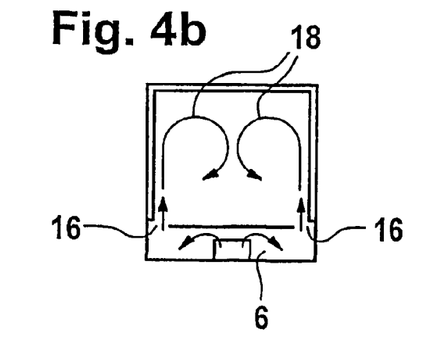
FIG. 4b shows a cross section of a variant b, along the line IV-IV in FIG. 3.
Figure 5:
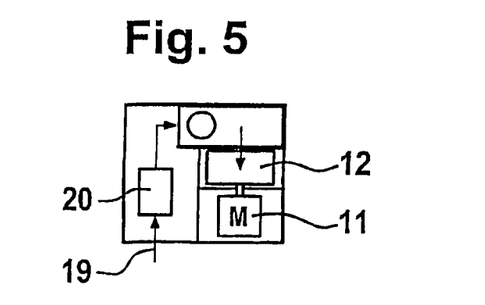
FIG. 5 shows a cross section along the line V-V in FIG. 3.
Figure 6A:
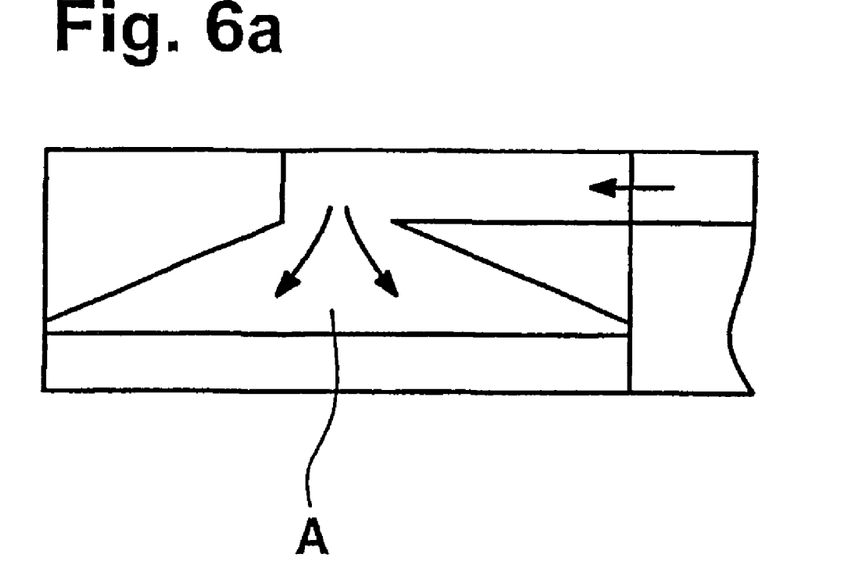
FIG. 6a shows a cross section of the variant a in FIG. 4a, along the line VI-VI in FIG. 3.
Figure 6B:
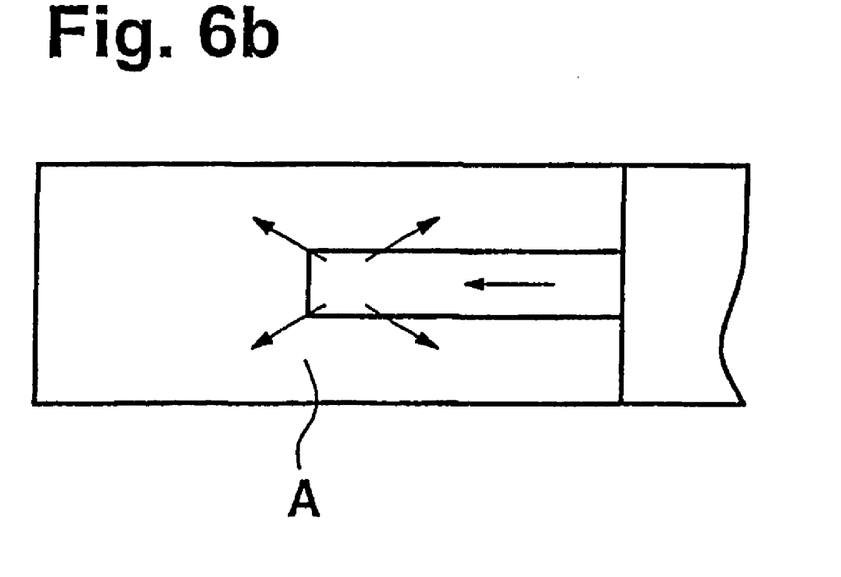
FIG. 6b shows a cross section of the variant b in FIG. 4b, along the line VI-VI in FIG. 3.

FIGS. 3 through 5 show a slightly different embodiment which is distinguished from the embodiment in FIG. 1 primarily through the outer geometry of the incubator. A motor 11 drives a fan 12 which ensures air circulation in the direction of the arrows. The air is passed across a heating/humidifying device 13 and a sensing device 14 which measures temperature and air humidity. On the basis of the corresponding signals, the incubator is then regulated with the aid of a microprocessor 15. The air which is circulated is blown into the stabilizing space A under the support surface 5 (FIGS. 3 and 6) as is indicated in FIG. 4a, and laterally via a corresponding wall 17 into the patient space. FIG. 4b shows another possible solution in which the air from the stabilizing space A is blown in through the gaps 16 on both longitudinal sides of the patient space and two cylinders of air are formed. Through the gap 16 under the wall 17, the overpressure in the stabilizing space is generated for the necessary flow speed needed to create the cylindrical flow 18 in the patient space 1. The air then passes back into the air delivery part 7 and is blown back in again.

The air delivery part 7 shown diagrammatically is designed as a Venturi tube at whose narrowest cross section the suction opening for fresh air 19 through the filter 20 is arranged. As is indicated by the arrow 19 in FIG. 5, fresh air is continuously suctioned off and, if necessary, oxygen added via a filter 20 in order to replenish the air, while the used air escapes through openings (not shown), for example in the area of the cover 4 which is made of transparent plastic. Part 9 contains the operating panel and the control and monitoring devices, while part 10 contains the connections for electrical power and, if appropriate, gas.

A measurement coil appropriate to the examination method and to the purpose of the examination is introduced through the hatch 8 into the patient space. The cable connecting the coil to the tomograph is routed through an opening 24 in the hatch 8. Infusion lines, anesthesia lines and measurement cables can also be routed through the opening 24 in the end wall of the enclosure.

An oxygen saturation $SpO_2$ sensor (cable and sensor not shown) can be attached at 25 and routed through the opening 24 to the patient. The measurement is effected via optical waveguides in order to rule out disturbances for the NMRI tomograph.

Figure 7:
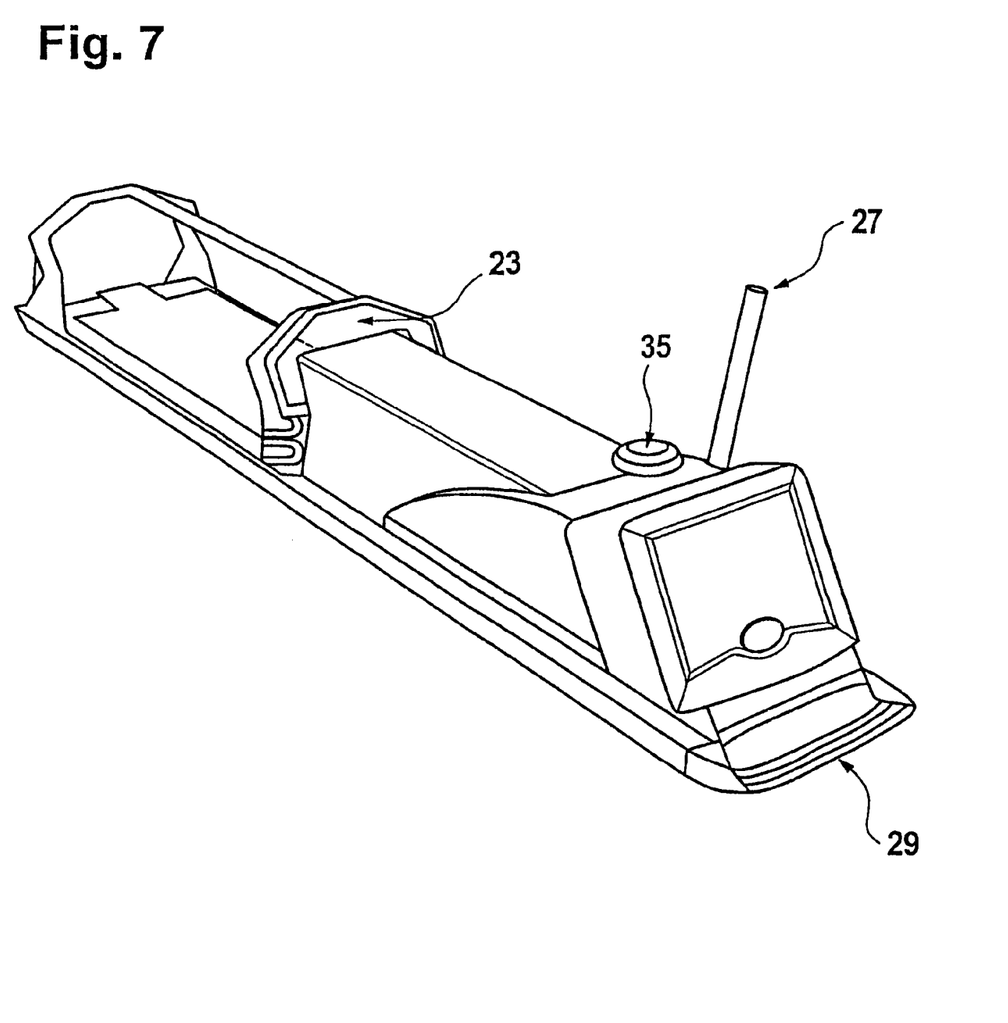
FIG. 7 shows, in a perspective view, a third embodiment of the incubator according to the invention.
Figure 8:
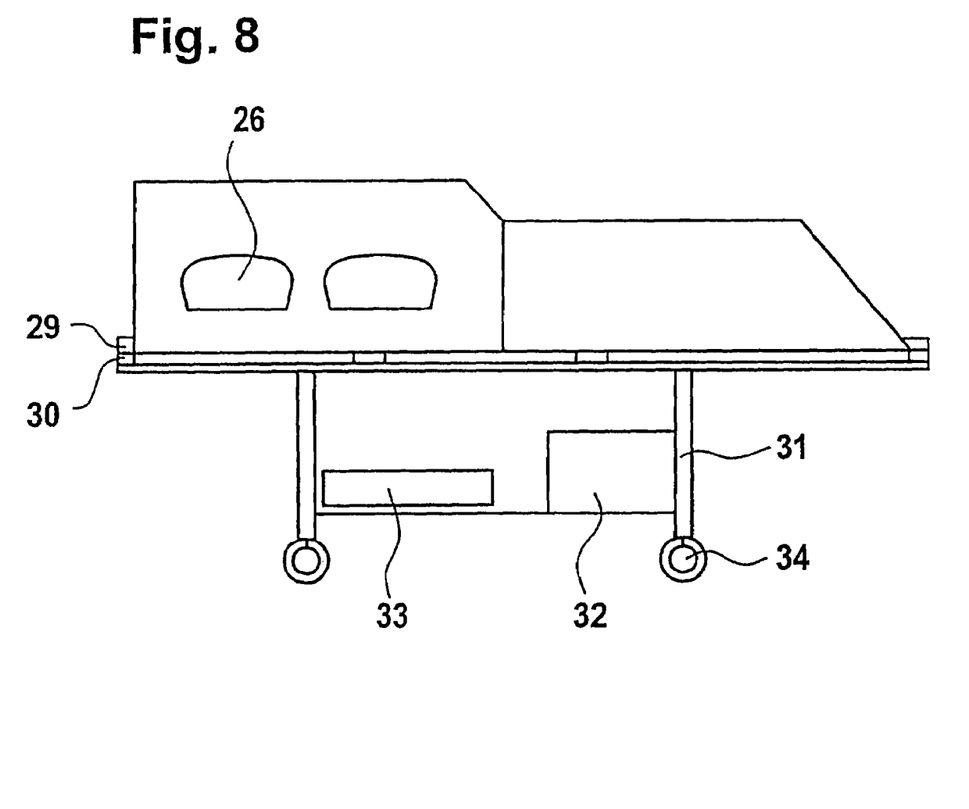
FIG. 8 shows a side view of the incubator placed on a trolley.

FIG. 7 shows another embodiment in which an additional window 23 is provided at one end face of the receiving space 1. A rod 27, for attachment of infusion lines, and handgrips 29 are also provided. The handgrips at the same time serve as an interface for attaching the appliance to a trolley 28. FIG. 8 shows the structure of the MR-compatible trolley 28 consisting of gas supply 33, uninterruptible power supply 32 and spring suspension 31. The wheels 34 can be steered and fixed and are as large as possible in order to compensate for irregularities of the floor. The mount 30 ensures a secure connection between incubator and trolley 28 during transport.

Figures 9, 9A:
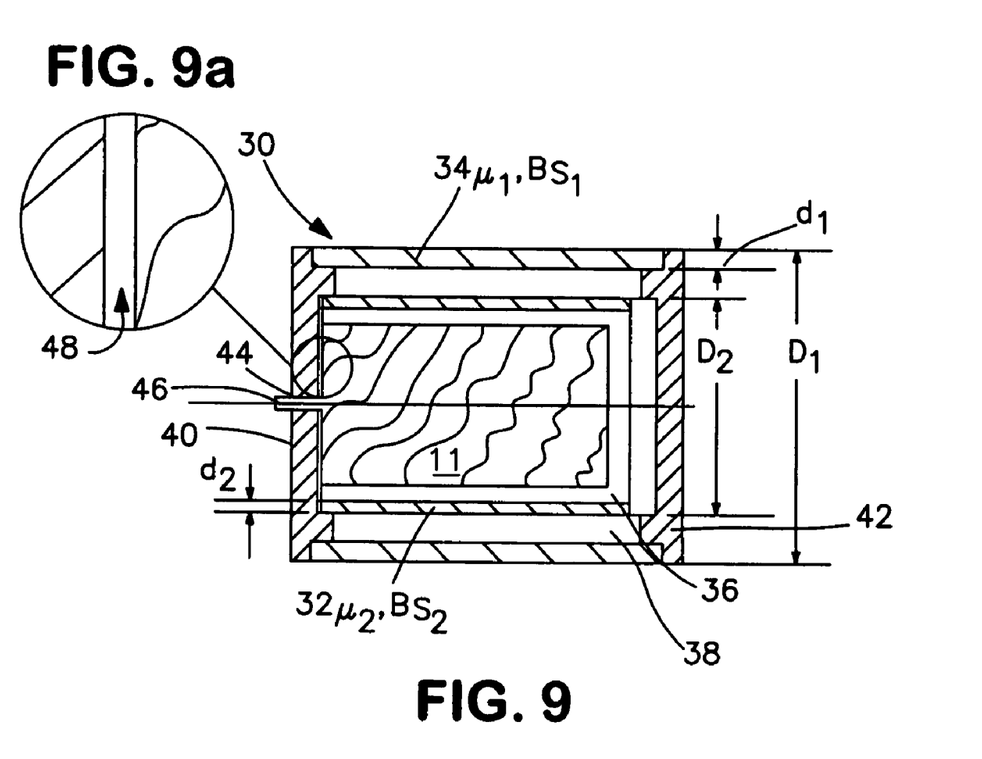
FIG. 9 is a sectional view through an electric motor shielded according to aspects of the present invention.
FIG. 9a is an enlarged portion of FIG. 9 showing a dielectric gap between the motor and an end cap of the shield.
Figure 10:
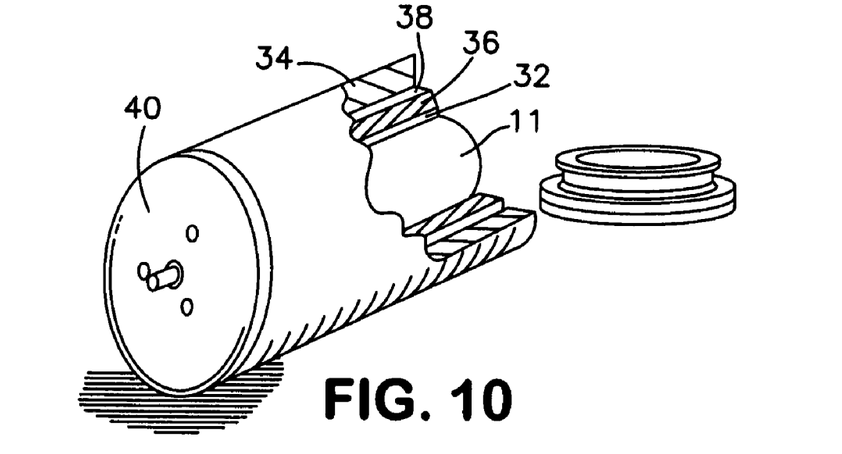
FIG. 10 is an exterior perspective view, partially broken away, of the shielded electric motor of FIG. 9.

FIGS. 9, 9a and 10 illustrate a shielding configuration for the electric motor 11. A shielding assembly 30 constructed of soft magnetic material surrounds the motor 11 to prevent the magnetic field of the imaging instrument from disrupting operation of the motor. The shielding assembly includes inner and outer cylindrical shields 32, 34. Each of the inner and outer cylindrical shields 32, 34 has a diameter D2, D1, and a thickness d2, d1, respectively. The shields 32, 34 must be thick enough to have structural integrity, but not excessively thick, because large bodies of ferromagnetic material would interfere with the functioning of the imaging equipment. Effective thicknesses d2, d1 for the shields 32, 34 are between $\frac{1}{10}^{th}$ and $\frac{1}{20}^{th}$ of the diameter D2, D1 of the shield. The shields 32, 34 are configured to surround the motor and leave an air gap 36 between the motor 11 and the inner cylindrical shield 32. A further air gap 38 is defined between the inner and outer cylindrical shields 32, 34.

End caps 40, 42 close the ends of the shielding assembly 30. One end cap 40 provides an opening 44 for the shaft of the motor 46. The motor 11 is secured within the shield assembly 30 by screws passing through the end cap 40 and a plastic ring or disc to engage the motor 11. This arrangement provides a dielectric gap 36, 38, 48 (plastic/air) between the motor 11 and the shielding assembly. This dielectric gap 36, 38, 48 isolates the motor from the magnetic circuit induced in the shield assembly 30 by the magnetic field of the imaging equipment. The screws may be of a plastic material to further isolate the motor 11. Experimentation has shown that two shielding cylinders having thicknesses d2, d1 separated by an air gap are more effective than one cylinder having a thickness equal to d2+d1.

In a preferred embodiment, the saturation induction BS1 of the outer shield 34 should be greater than the saturation induction BS2 of the inner shield 32, while the permeability μ2 of the outer shield 34 should be less than the permeability μ1 of the inner shield 32. This arrangement improves the shielding effect by directing the magnetic lines of flux of the imaging instrument magnetic field around the motor 11.

Soft magnetic materials suitable for the disclosed shield assembly 30 are iron and iron alloys. Alloy content and treatment of the metal effect the saturation induction and permeability properties of the materials. Similar arrangements can be used to shield other electronic components of the incubator, although the ferromagnetic content of the incubator should be minimized.

While preferred embodiments of the foregoing invention have been set forth for purposes of illustration, the foregoing description should not be deemed a limitation of the invention herein. Accordingly, various modifications, adaptations, and alternatives may occur to one skilled in the art without departing from the spirit and the scope of the present invention.

What is claimed is:

1. A newborn and premature patient incubator for use in a magnetic field generated by medical imaging equipment, said incubator comprising:
   a patient-receiving enclosure partially defined by a movable hood;
   an air delivery unit including a heating/humidifying device and an electric motor to circulate air through the patient receiving enclosure;
   a control unit including a sensing device arranged to measure air temperature and humidity in said patient-receiving enclosure, said control unit operatively connected to said air delivery unit;
   a control panel operatively connected to said control unit permitting the selection of a temperature and humidity to be maintained in said patient-receiving enclosure by said control unit and air delivery unit; and
   a shielding body of soft magnetic material surrounding and spaced apart from said electric motor to define a dielectric gap between said motor and said shielding body,
   wherein said air delivery unit, control unit and control panel are arranged integrally on the incubator and the incubator can be placed in the magnetic field of the medical imaging equipment.

2. The newborn and premature patient incubator of claim 1, wherein said shielding body comprises an outer shielding body and an inner shielding body said inner and outer shielding bodies spaced apart from each other to provide a dielectric gap between said inner and outer shielding bodies.

3. The newborn and premature patient incubator of claim 2, wherein the soft magnetic material of said outer shielding body has a saturation induction greater than a saturation induction of the soft magnetic material of said inner shielding body.

4. The newborn and premature patient incubator of claim 3, wherein the soft magnetic material of the outer shielding body has permeability that is less than a permeability of the soft magnetic material of the inner shielding body.

5. The newborn and premature patient incubator of claim 1, wherein said dielectric gap is partially provided by a plastic material supporting said motor relative to said shielding body and a remainder of said dielectric gap comprises an air gap between said motor and said shielding body.

6. The newborn and premature patient incubator of claim 1, wherein said shielding body comprises a cylindrical portion having opposite ends each closed by a disc-shaped cover, one of said disc-shaped covers including a hole allowing a shaft of said motor to protrude from said shielding body.

7. The newborn and premature patient incubator of claim 1, wherein said shielding body includes a generally cylindrical wall having a diameter D and a thickness d, a ratio of said diameter D to said wall thickness d (D/d) should be at least 10 and no greater than 20.

8. The newborn and premature patient incubator of claim 1, comprising devices for delivery of oxygen.

9. The newborn and premature patient incubator of claim 1, comprising devices for regulating the oxygen concentration of the air delivered to the patient.

10. The newborn and premature patient incubator of claim 1, comprising at least one measurement coil for magnetic resonance is arranged in the patient space.

11. The newborn and premature patient incubator of claim 10, wherein the at least one measurement coil is adjustable relative to a patient in the patient space.

12. The newborn and premature patient incubator of claim 10, wherein the at least one measurement coil can be introduced and removed from said patient-receiving enclosure through an end wall of said enclosure, without the patient having to be moved.

13. The newborn and premature patient incubator of claim 1, wherein said air circulation device includes a fan operatively coupled to said electric motor.

14. The newborn and premature patient incubator of claim 1, wherein said control device comprises a microprocessor.

15. The newborn and premature patient incubator of claim 1, wherein said patient-receiving enclosure is further defined by an end wall and said end wall is provided with passages for ventilation lines, anaesthesia lines, infusion lines and signal cables.

16. The newborn and premature patient incubator of claim 1, wherein said hood is transparent to permit observation of the patient.

17. The newborn and premature patient incubator of claim 1, wherein fresh air is drawn into said patient-receiving enclosure by an underpressure generated by a Venturi tube.

18. The newborn and premature patient incubator of claim 1, comprising a transparent window on an end face of the patient-receiving enclosure.

19. The newborn and premature patient incubator of claim 1, comprising at least one device to measure oxygen saturation in the patient.

20. The newborn and premature patient incubator of claim 1, comprising a trolley including a backup power supply and a gas supply configured to function when placed in the magnetic field of the medical imaging equipment.

* * * * *